United States Patent [19]

Walaszek et al.

[11] Patent Number: 4,845,123

[45] Date of Patent: Jul. 4, 1989

[54] REDUCTION IN VIVO OF THE INAPPROPRIATE LEVELS OF ENDOGENOUS AND ENVIRONMENTAL-DERIVED COMPOUNDS BY SUSTAINED-RELEASE INHIBITORS OF β-GLUCURONIDASE

[75] Inventors: Zbigniew Walaszek; Malgorzata Hanausek-Walaszek; Thomas E. Webb; John P. Minton, all of Columbus, Ohio

[73] Assignee: The Ohio State University, Columbus, Ohio

[21] Appl. No.: 762,339

[22] Filed: Aug. 5, 1985

[51] Int. Cl.$^4$ .............................................. A61K 31/19
[52] U.S. Cl. .................... 514/473; 514/470; 514/574
[58] Field of Search ................ 424/10; 514/470, 473, 514/574

[56] References Cited

U.S. PATENT DOCUMENTS 3,928,583 12/1975 Furuno et al. ...................... 424/180

FOREIGN PATENT DOCUMENTS 1066885 4/1967 United Kingdom .

OTHER PUBLICATIONS

Furuno et al., Chemical Abstracts, 84,115903y (1976).
Furuno et al., Chemical Abstracts, 85,154048p (1976).
Levvy, Biochem. J., 52:464–470 (1952).
Boyland et al, Invest. Urol., 2:439–445 (1965).
Bradley, J. Urol., 88:626–628 (1962).
Iida et al, Jpn J. Pharmacol., 15:88–90 (1965).
Miyakawa et al, Invest. Urol., 10:256–261 (1973).
Uemura et al, Nishi Hippon Hinyokika, 37:327–342 (1975), Chem. Abstr., 86:41460u, 1977.
Takada et al, Cancer Res., 42:331–334 (1982).
Boyland et al, Brit. J. Urol., 36:563–569 (1964).
Katayama, Jpn. J. Urol., 63:951–971 (1972).
Walaszek et al, Carcinogenesis, 5:767–772 (1984).
Zedeck et al, Eds., Inhibition of Tumor Induction and Development, Plenum Press, New York, Ch. 9:219 (1981).
Willett et al, N. Eng. J. Med., 310:430–434 (1984).
Walaszek et al, AACR Abstracts, vol. 35, No. 507 (1984).

Primary Examiner—Earl Nielsen
Attorney, Agent, or Firm—Emch, Schaffer, Schaub & Porcello Co.

[57] ABSTRACT

A method for the reduction in vivo of the inappropriate levels of endogenous and environmental-derived compounds by inhibiting the activity of β-glucuronidase in a mammal which comprises the administration to the mammal of an effective amount of a water insoluble, or sparingly soluble, sustained release precursor of glucarolactone or its analog is disclosed. The sustained release precursor of glucarolactone compound is selected from the group consisting of D-glucaric acid, D-galactaric acid, and L-idaric acid or derivatives or analogs. An orally administrable preparation of the sustained release precursor of glucarolactone compound is provided in the form of a capsule or tablet, such that the glucarolactone or its analog is slowly released in the stomach of the treated animal or human.

27 Claims, 4 Drawing Sheets

REDUCTION IN VIVO OF THE INAPPROPRIATE LEVELS OF ENDOGENOUS AND ENVIRONMENTAL-DERIVED COMPOUNDS BY SUSTAINED-RELEASE INHIBITORS OF β-GLUCURONIDASE

BACKGROUND OF THE INVENTION

This invention relates to the inhibition of chemical toxicity and carcinogenesis by sustained release derivatives of D-glucaro-1,4-lactone. D-glucaro-1,4-lactone is a naturally occurring compound and is known to be a potent inhibitor of β-glucuronidase in vitro (Levvy, G. A. *Biochem. J.,* 52:464–470, 1952). It is known that most chemical carcinogens and tumor promoters are trapped in the form of a glucuronide, which is then excreted from the body. This process, glucuronidation, is a principal conjugation pathway in vertebrates. The conjugates of xenobiotics, including carcinogens and promoters, are excreted via the bile and urine. The elimination of potentially damaging chemicals which undergo glucuronidation is not only limited by their rate of conjugation with glucuronic acid, but also by their rate of de-glucuronidation by the ubiquitous enzyme β-glucuronidase, which hydrolyzes the carcinogen-glucuronide conjugate, and thereby frees the carcinogen to inflict damage and produce neoplastic transformations.

Glucuronyl transferase, which catalyzes glucuronidation (a major pathway of detoxification), and β-glucuronidase, which catalyzes de-glucuronidation, appear to be present in all mammalian tissues. Thus, any factor which alters the ratio of these two enzymes may alter the susceptibility of the target tissue to chemical carcinogens or promoters.

Chemical carcinogenesis exhibits two main steps in the multi-step process of tumorigenesis, an irreversibly initiating phase and a subsequent reversible promotion phase. These two phenomena are discrete and temporally separable. Since the identification of experimental promoting agents such as croton oil in skin carcinogenesis, phenobarbital in hepatocarcinogenesis, and saccharin in bladder carcinogenesis, a major focus of carcinogenesis is now on the promotion phase of chemical carcinogenesis. The elimination or reduction of all environmental and endogenous carcinogens and promoters to which the human populations are at risk presents a formidable task. The identification of nontoxic inhibitors of one of the phases of the carcinogenic process, particularly those of natural origin, are most relevant to this problem.

As one example, polynuclear aromatic hydrocarbons (PAHs) are widespread environmental pollutants, which occur in the atmosphere, water and food and also in tobacco smoke. PAHs are strongly suspected of causing cancer in man. Primary metabolites of PAHs, such as epoxides, dihydrodiols and phenols as well as their secondary metabolites such as diol-epoxides are detoxified through coupling with glutathione, sulfuric acid and glucuronic acid. Also, certain toxic chemicals, such as TCCD (dioxin) are known to undergo glucuronidation in the body. It is known that conjugation with glucuronic acid, i.e. glucuronidation, is the principal conjugating pathway in vertebrate species examined over a wide range of tissues and accounts for most of the conjugated detoxified material in bile and urine. Thus, although D-glucaro-1,4-lactone appears to be present in all tissues and fluids of the body, it is thought to be of limited value in vivo since it is only present in low concentrations in subpopulations thought to be at high risk for cancer, and is cleared from the body too rapidly to be very effective.

In the past, attempts have been made to use GL to prevent the experimental induction of bladder cancer with 2-naphthylamine in dogs (Boyland et al., *Invest. Urol.,* 2:439–445 1965), however without any success. The use of GL was based on the concept of inhibition of the enzyme β-glucuronidase in mammalian urine and thus prevention of enzymic hydrolysis of glucuronides of 2-naphthylamine carcinogenic metabolites in the bladder. A similar attempt using 2-acetylaminofluorene as a carcinogenic agent with GL in rats, was also unsuccessful (Bradley, *J. Urol.,* 88:626–628, 1962). GL was rapidly metabolized and less than 50% of the administered compound was excreted unchanged in urine and the excretion was also rapid. GL in both of the experiments cited above was given to animals at the same time as carcinogens, i.e. too late to be effective.

The European Pat. No. 1,066,885 shows the use of 2,5-di-O-acetyl-D-glucosaccharo-1,4-3,6-dilactone (DAGDL), a synthetic precursor of GL, as a therapeutic agent for the treatment of several diseases, such as diabetes, rheumatoid arthritis, toxemia in pregnancy and bladder cancer. However, a review of the medical literature shows that the attempts to use DAGDL in the treatment of such diseases were unsuccessful. For example, the effect of 2,5-di-O-acetyl-D-glucaro-1,4;6,3-dilactone (DAGDL), a potent in vivo β-glucuronidase inhibitor (Iida et al., *Jpn. J. Pharmacol.,* 15:88–90, 1965) on the induction of bladder tumor with 2-acetylaminofluorene (2-AAF) was studied in rats (Miyakawa et al., *Invest. Urol.,* 10:256–261, 1973). Again, DAGDL was given to animals at the same time as the carcinogen 2-AAF, and statistical analysis of the tumor incidence data did not disclose any significant difference between DAGDL-treated and control rats.

An attempt to inhibit, with DAGDL, N-butyl-N-(4-butanol)nitrosaminemediated induction of bladder tumor in the rat was also unsuccessful (Uemura et al., *Nishi Nippon Hinyokika* 37:327–342, 1975; *Chem. Abstr.,* 86:41460u, 1977).

In a recent study, a synthetic inhibitor of β-glucuronidase failed to reduce tumor incidence in azoxymethane-induced colonic carcinogenesis in rats (Takado et al., *Cancer Res.,* 42:331–334 1982) because it was administered at the same time as a carcinogen.

A clinical trial of GL in an attempt to prevent the development of bladder tumors in patients, who had previously had bladder cancer, failed to show any clear beneficial effects of GL (Boyland et al., *Brit. J. Urol.,* 36:563–569, 1964). A similar trial using DAGDL instead of GL showed only a slight beneficial effect (Katayama, *Jpn. J. Urol.,* 63:951–971, 1972). In these studies GL or DAGDL were used as chemotherapeutic agents rather than as anti-carcinogens.

Use of DAGDL to increase clearance of antibiotics which cause kidney damage (Furuno et al., U.S. Pat. No. 3,928,583, 1975) showed inconclusive results.

The above prior uses expressly illustrate that DAGDL and GL, were not effective as therapy in the treatment of various existing diseases, such as cancer, since the DAGDL or GL compounds were administered after the disease was already present in the subject.

Walaszek, et al., *Carcinogenesis*, 1984, 5:767-772, showed the use of DAGDL, as an inbititor of the initiation phase of carcinogenesis where the initiation of a tumor, caused by exposure to the carcinogen 7,12-dimethylbenzanthracene (DMBA), was inhibited by the administration of DAGDL. It was disclosed that the inhibition of $\beta$-glucuronidase increased the proportion of the carcinogen DMBA which was sequestered and excreted as the glucuronide and decreased the proportion of the carcinogen available for activation of the proximal carcinogen; however, there was no indication that DAGDL could also act to inhibit the totally unrelated promotion phase of carcinogenesis since the promotion phase of carcinogenesis most often occurs at a later period in time, often years after the initiating event of exposure to the carcinogen. Further, since DAGDL is a synthetic compound, it would not be widely accepted by the consuming public for use in the prevention of the initiating phase of carcinogenesis.

Therefore, there is a need for anticarcinogenic agents and antipromoters which will show sustained in vivo activity.

There is a further need for inhibitors of chemical toxins and carcinogens which undergo glucuronidation in the body and are acceptable to the general population.

There is a further need for reducing cancer incidence in high risk subpopulations by administration of sustained release precursors of GL in order to raise the body levels of GL.

SUMMARY OF THE PRESENT INVENTION

The present invention relates to the use of slow release precursors of glucarolactone (GL) in order to inhibit the activity of the $\beta$-glucuronidase enzyme. The invention further relates to a method for significantly reducing, by interrupting the initiation and promotion phases of carcinogenesis, the incidence of chemically induced or promoted cancer. The invention further relates to providing the sustained release precursors of GL to subpopulations exposed to carcinogens and promoters by incorporating the $\beta$-glucuronidase inhibitor precursors, in suitable vehicles such as vitamin-type capsules, tablets, suspensions or food additives.

The slow or sustained release precursors of glucarolactone (GL) are 2,5-di-O-acetyl-D-glucaro-1,4;6,3-dilactone or DAGDL, a synthetic derivative of GL; calcium glucarate (CGT); potassium hydrogen D-glucarate (PGT); and microencapsulated GL (EGL). These compounds are non-toxic, can be taken by mouth, and their conversion to GL occurs primarily in the stomach. In addition, the latter three are naturally occurring compounds.

The invention provides for the administration of the sustained or slow release precursors of GL. These precusor compounds, upon conversion in vivo to GL, decrease the amount of carcinogen available for activation to the proximal carcinogen. Pretreatment with the sustained release precursors of GL dramatically reduce the toxicity and carcinogenic activity of a wide range of carcinogens of varying structures, include environmental carcinogens such as polycyclic aromatic hydrocarbons, nitrosamines, aromatic amines, fungal toxins, polychlorinated biphenyls and dioxins. The sustained release precursors, by conversion to GL, also inhibit the promotion phase of chemical carcinogenesis as, for example, in sex hormone-mediated promotion of certain cancers. The precursor compounds decrease the amount of such "promoters" of sex-hormones and catecholamines available to activate or trigger the injured, cancer-initiated cells to become carcinogenic.

It is an object of this invention to prevent the inappropriate and detrimental process of de-glucuronidation by inhibiting the $\beta$-glucuronidase enzyme with the sustained release precursors of GL during the critical hours immediately after exposure to a carcinogen.

It is a further object of this invention to reduce the toxicity of various compounds which undergo glucuronidation by inhibiting the activity of the $\beta$-glucuronidase enzyme, either immediately prior to or after exposure to such toxic compounds, through the administration of the sustained release precursors of GL.

It is a further object of this invention to increase excretion of a carcinogen and/or a promoter by inhibiting $\beta$-glucuronidase activity with the administration of the sustained release precursors of GL, and thereby increase the excretion of the carcinogen-glucuronide conjugate from the body.

It is a further object of this invention to utilize the sustained release precursors of GL in tests for carcinogenicity.

It is a further object of this invention to prevent and/or treat steroid dependent cancers, as well as other diseases caused by steroid hormone disorders, by lowering the level of such hormones in the body through the administration of the sustained release precursors of GL.

Other objects, as well as aspects and advantages of the present invention will become apparent from a study of the specification.

DESCRIPTION OF THE PREFERRED EMBODIMENT

Figure 1:
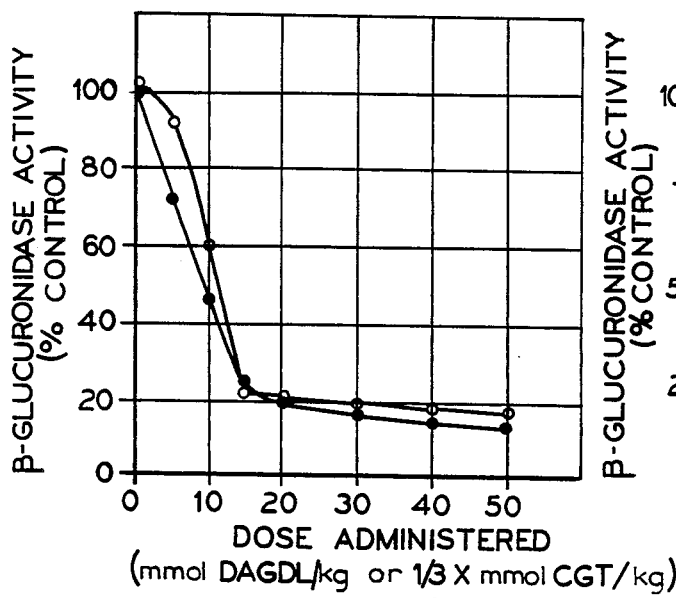
FIG. 1 is a dose-response graph showing the inhibition of serum $\beta$-glucuronidase activity which was assayed 1 hour after the administration of DAGDL (●—●) or 3 hours after the administration of CGT (O—O).

The present invention relates to sustained release precursors of glucarolactone (GL) or its analogs which, according to the present invention, act to inhibit β-glucuronidase activity. The administration of the precursors of GL are useful in reducing the toxicity of any such compounds which undergo glucuronidation.

The sustained release precursors of GL are administered prior to, during or after exposure to chemicals carcinogens. These β-glucuronidase inhibitors are useful in preventing the initiation phase of carcinogenesis. In addition, they can be used to prevent promotion of carcinogenesis and tumorigenesis. Further, the β-glucuronidase inhibitors can be administered to tumor bearing mammals or poultry to arrest growth of tumors or to cause regression of a tumor.

The de-glucuronidation inhibitors or precursors thereof are preferably D-glucaric acid, D-galactaric acid, L-idaric acid or derivatives or analogs thereof. The de-glucuronidation inhibitors are insoluble or only sparingly soluble in water at pH 5–7 but will go into a solution at pH of 1–4. The de-glucuronidation inhibitors are preferably administered intragastrically. The inhibitors can then be delivered in a capsule or tablet form for slow release upon digestion in the stomach. Alternatively, the β-glucuronidase inhibitors can be administered as an implant to provide sustained release of the glucuronidation inhibitors. In addition, the inhibitors can be administered in food as a food additive.

An example of conversion, in vivo to D-glucaro-1,4-lactone (GL) of the precursor 2,5-di-O-acetyl-D-glucaro-1,4;6,3-dilactone (DAGDL) is as follows:

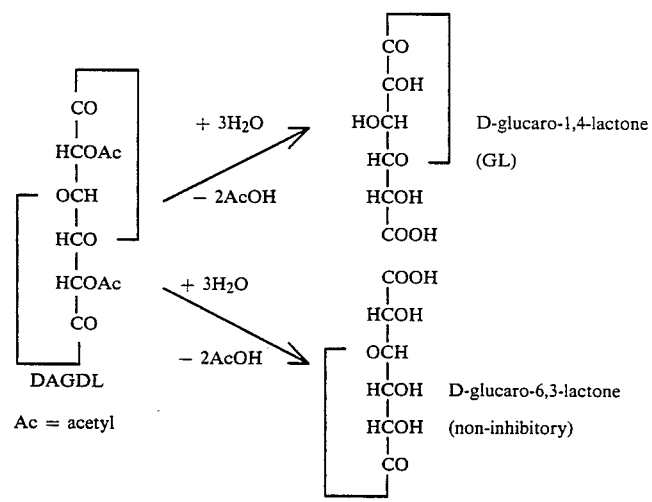

An example of the conversion, in vivo, to D-glucaro-1,4-lactone (GL) of the precursor calcium glucarate (CGT) is as follows:

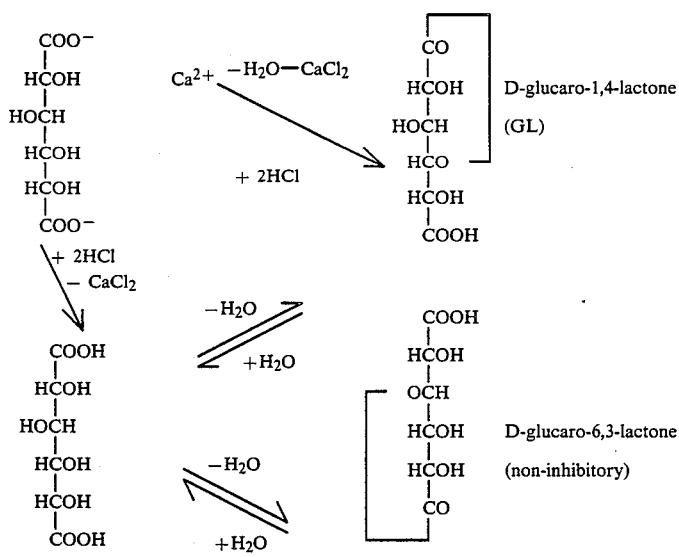

The inhibitors also reduce the toxic effects of any such compounds which undergo glucuronidation. The β-glucuronidase inhibitors cause the increased excretion of a toxin- or carcinogen-glucuronide conjugate by inhibiting the β-glucuronidase enzyme which when uninhibited, hydrolyses the conjugate thereby freeing the toxin or carcinogen to inflict damage and produce neoplastic transformation.

The cancer initiating agents which cause the body to produce and activate the β-glucuronidase enzyme activity are chemicals, radiation exposure, viruses and/or oncogenes. The initiated cells must then be subjected over a period of time to promotion by tumor promoters which can either be of exogenous or endogenous origin, such as steroid hormones or catecholamines. The β-glucuronidase inhibitors cause the increased excretion of promoter-glucuronide conjugates.

It is known that various known carcinogens have been shown to induce the 60 kd oncofetal protein in normal rats within 3 weeks of treatment. This 60 kd protein is also produced by all of the over 100 human and animal tumors studied and by fetal tissue. The 60 kd oncofetal protein is released to the blood by both tumors and by normal tissues exposed to carcinogens, therefore, it is practical to monitor its concentration in the blood plasma. The factor has been assayed by its ability to induce the release (transport) of messenger-like RNA from isolated nuclei. In this respect it is similar to the 35 kd messenger RNA transport factor present in normal adult tissue, and which co-exists with this 60 kd oncofetal form in tumors and fetal tissues.

As monitored in the blood plasma, the production of the 60 kd protein in carcinogen-treated rats proceeds in two phases. During the early phase, the 60 kd factor is transiently induced in the carcinogen-treated rat, its plasma concentration peaking at approximately 21 days. This is followed, in rats developing tumors, by a second extended phase which parallels tumor growth.

Thus, the level of the 60 kd factor in the plasma provides an effective means of evaluating the effectiveness of the sustained release precursors of the endogenous β-glucuronidase inhibitor GL on chemical carcinogenesis. The suppression of the carcinogen-mediated induction by anti-carcinogens shows that this induction is closely associated with the initial stages of carcinogenesis. Also there is a quantitative relationship between carcinogen exposure and the initial induction of carcinogenesis.

As shown by the following examples, the sustained release precursors of GL are effective in inhibiting the activity of β-glucuronidase, and therefore in inhibiting chemical toxicity and carginogenesis.

EXAMPLE I

The following carcinogens were administered intraperitoneally (i. p.) in 0.5 ml of sesame oil (or 0.9% saline, pH 5.0 in the case of nitroso-derivatives) to 50 day old female rats of the Sprague Dawley strain (controls received the vehicle only): Benzo[a]pyrene, 210 μmoles/kg; 7,12-dimethylbenz[a]anthracene, 160 μmoles/kg; 2-acetylaminofluorene, 200 μmoles/kg; 2-naphthylamine, 500 μmoles/kg; N-nitroso-N,N-dibutylamine, 760 μmoles/kg; N-nitroso-N-methylurea, 440 μmoles/kg; N-nitroso-N-ethylurea, 600 μmoles/kg; aflatoxin $B_1$, 10 moles/kg intragastrically (i.g.); aflatoxin $G_2$, 10 μmoles/kg; N-nitroso-N,N-dimethylamine, 135 μmoles/kg; N-nitroso-N, N-diethylamine, 1.0 mmole/kg; 1,2-dimethylhydrazine, 560 μmoles/kg; 1-nitropyrene, 105 μmoles/kg; 3-methylcholanthrene, 160 μmoles/kg and safrole, 600 μmoles/kg. All carcinogens but one were purchased from Sigma Chemical Company, St. Louis, MO. 1-Nitropyrene was obtained from the Aldrich Chemical Company, Milwaukee, WI.

Figure 2:
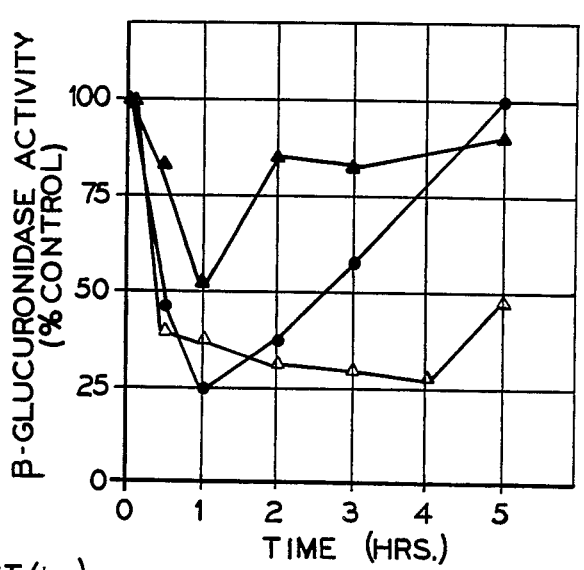
FIG. 2 is a time-course graph showing serum $\beta$-glucuronidase inhibition by GL and slow-release forms thereof, wherein the inhibition following a single i.g. dose (1.5 mmoles/kg) of GL (▲—▲) or EGL (Δ—Δ) or DAGDL (●---●) is shown.
Figure 3:
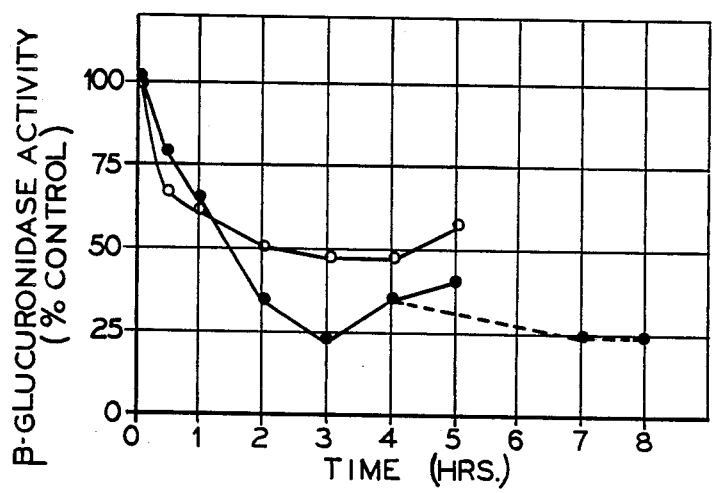
FIG. 3 is a time-course graph showing serum $\beta$-glucuronidase inhibition by glucaric acid salts, wherein the inhibition following a single i.g. dose (4.5 mmoles/kg) of CGT (●—●) and PGT (O—O) and the effect of a second dose of CGT given to rats at 2.5 hours is also shown (●—●) are shown.

GL was synthesized and microencapsulated to give sustained-release GL (EGL), by an established procedure used to microencapsulate ascorbic acid, as reported in Samejima, M. et al., Chem. Pharm. Bull., (Tokyo) 1982, 30:2894–2899. In this procedure, the GL as a fine powder is added to a stirred mixture of cyclohexane, polyisobutylene as coacervation-inducing agent and ethylcellulose as wall-forming material. The addition of GL is at 78° C., then phase separation is induced by lowering the temperature first to 40° C., then to 25° C. The microcapsules, which have thick walls, are washed with cyclohexane and dried. Microcapsules of 150–250 μm in diameter are selected by mechanical sieving. DAGDL, calcium D-glucarate (CGT), and potassium hydrogen D-glucarate (PGT) were synthesized. For comparison of efficacy of the inhibitors, 1,5 mmoles/kg (GL, EGL or DAGDL) or 4.5 mmoles/kg (CGT or PGT) of the inhibitor in 1.0 ml of sesame oil or vehicle only (controls) was administered to rats by stomach tube at zero time. Blood samples were obtained from different rats by cardiac puncture under ether anesthesia. The serum was prepared and assayed for β-glucuronidase activity using a commerical diagnostic kit sold by Sigma Chemical Company, St. Louis, MO. The assay is based on the hydrolysis of phenolphthalein-glucuronide and quantitation of phenolphthalein in alkaline medium at 550 λm. Dose-response curves and time course of the inhibition of serum β-glucuronidase are shown in FIGS. 1-3. For tests of anti-carcinogenicity, the inhibitors were administered by stomach tube in 1.0 ml of sesame oil 30 minutes before and again at 2.5 hours after the carcinogen, for DAGDL, or 3 hours and 30 minutes before the carcinogen, for EGL, CGT, and PGT. The controls received sesame oil only by stomach tube.

Blood was obtained from the rats under ether anesthesia by cardiac puncture using heparinized syringes and following removal of the cellular components the plasma was stored frozen until testing. All sampling was done 21 days post-carcinogen treatment.

In order to specifically quantitate the 60 kd factor it was necessary to separate the various RNA transport factors present in the plasma. The 30-60% ammonium sulfate fraction of the plasma was applied, after dialysis, to a 1.6×90 cm Sepharose CL-6B column in TMK buffer (50 mM Tris-HCl, (pH7.5) 25 mM KCl and 2.5 mM $MgCl_2$ and eluted with the same buffer. Three ml fractions were collected, of which 200 μl aliquots were assayed in the reconstituted cell-free system for RNA transport activity.

This assay measures the release of labeled RNA from 30 minutes prelabeled rat liver nuclei. The liver nuclear RNA is prelabeled in vivo with $[6-^{14}C]$ orotate. The system is dependent on a 35 kd factor in the liver cytosol and under sub-optimal concentrations of liver cytosol, i.e. 5.0 mg/ml of cytosol protein rather than the optimum of 10-20 mg/ml, the system becomes sensitive to and constitutes an assay for exogenous RNA transport factors. The cell-free assay system consists of prelabeled nuclei, cytosol, buffer, salts, spermidine, dithiothreitol, ATP and an ATP-regenerating system, and ribonuclease inhibitors. With or without addition of 200 μl of plasma fractions, the assay is incubated at 30° C. for 30 minutes before pelleting the nuclei and precipitating the RNA from the supernatant for radio-assay. Results are reported as percentage increase in nuclear RNA release upon addition of the test fraction. Since identical amounts (85 mg) of plasma protein were loaded on the Sepharose CL-6B column, all profiles were directly comparable.

The data shown in FIGS. 1-3, confirm the potent inhibitory effect of the slow (sustained)-release precursors and/or forms of GL or β-glucuronidase activity in the rat serum and the time-course of this inhibition. Shown in FIG. 1 are dose-response curves for DAGDL and CGT inhibition in vivo of serum β-glucuronidase in 50 day old female Sprague Dawley rats. The β-glucuronidase activity was assayed 1 hour after the administration of DAGDL (●—●) or 3 hours after the administration of CGT (O—O). Thus, the enzyme activity is reduced 50% at 1.0 mmoles/kg body weight, and by 80% at 1.5 mmoles/kg body weight by DAGDL and at 3.0 mmoles/kg and 4.5 mmoles/kg, respectively by CGT. In FIG. 2 the time-course curves of serum β-glucuronidase activity following the administration of 1.5 mmoles/kg of each of the inhibitors shows the transient nature of the inhibition by GL, the more prolonged inhibition by DAGDL and the markedly prolonged inhibition, i.e., in excess of 5 hours, by EGL. As shown in FIG. 3, CGT and PGT both cause prolonged inhibition of β-glucuronidase in vivo. CGT and PGT were tested at 4.5 mmoles/kg, i.e., 3 times that of GL or slow release forms of GL, since only one third of the glucarate is converted to GL. Thus, CGT, PGT and EGL give even more prolonged inhibition than does DAGDL. These data are physiologically significant since an analysis of liver, kidney and lung β-glucuronidase activity shows that tissue activity parallels blood activity. Also, carcinogen co-administration does not significantly affect the degree of inhibition of β-glucuronidase activity by these inhibitors.

Following chromatography of the plasma on Sepharose CL-6B, the column fractions are assayed in the cell-free system consisting of 30 minute in vivo prelabeled nuclei in surrogate cytoplasm, which is sub-optimal only with respect to RNA transport factors. Two RNA releasing factors are observed in normal rat plasma, with molecular weights of 35,000 and 700,000 daltons, but only the 35 kd factor is considered to be the true component, the 700 kd component being an aggregate formed during fractionation procedures. Additionally, in the plasma of the tumor-bearing or carcinogen-treated rat, a 60 kd factor is present which exhibits similar, but not identical RNA transport activity.

Figure 4:
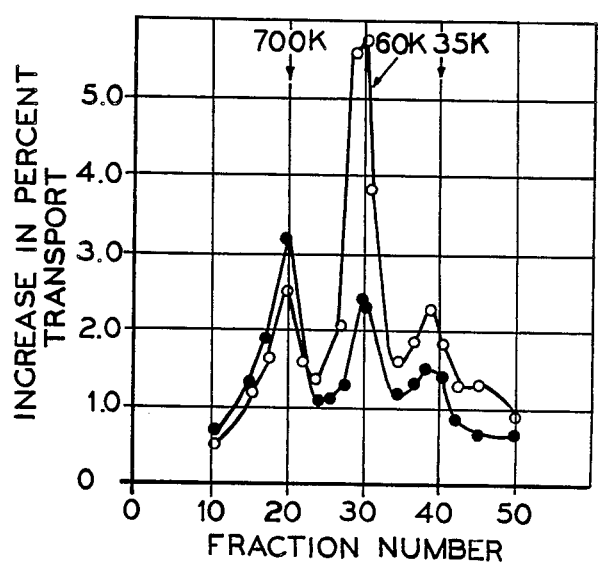
FIG. 4 is a graph showing Sepharose CL-6B profiles of the RNA-transport activities in the plasma of carcinogen-treated rats 21 days post-treatment wherein the profiles shown are those following treatment with N-nitrosodibutylamine, with (●—●) or without (O—O) concurrent treatment with CGT.

Shown in FIG. 4 is the Sepharose CL-6B profile of RNA releasing (transport) activity in the plasma of a rat treated with a carcinogenic dose of N-nitroso-N,N-dibutylamine with or without concurrent treatment with CGT. The data indicate that CGT pre-treatment resulted in over a 50% decrease in induction i.e., in the plasma concentration of the 60 kd factor.

The data in Table 1 summarize the results of an analysis of the effect of the β-glucuronidase inhibitors on the induction of the 60 kd factor by 15 known carcinogens of differing structure. The data indicate that the inhibitors consistently reduced the induction of the 60 kd factor, presumably as a result of suppression of carcinogenicity. The metabolites of all of the carcinogens listed in Table 1 may become glucuronidated at some point in their metabolism in the rat. This is, in fact, known to be true for the following carcinogens listed in Table 1: Safrole, BP, DMBA, 2-acetylamino-fluorene, 2-naphthylamine, N-nitroso-N,N-dibutylamine, aflatoxins, and 1-nitropyrene. The increased clearance resulting from increased net glucuronidation results in a reduction in their degree of carcinogenicity as evidenced by the 40-85% reduction in the percent depression in 60 kd factor induction.

The data in Example I indicate that DAGDL, CGT, PGT and EGL, upon slow conversion in vivo to GL and/or its release, decrease the amount of carcinogen available for activation to the proximal carcinogen. Pre-treatment with the sustained-release precursors and/or forms of GL dramatically reduces the toxicity and carcinogenic activity of a wide range of carcinogens of varying structures, including environmental carcinogens such as polycyclic aromatic hydrocarbons and their nitro-derivatives, nitrosamines, aromatic amines, and fungal toxins.

TABLE 1
Inhibition of the Induction of the 60 kd Factor Three Weeks Post-Treatment with Carcinogens

| Carcinogen | Inhibitor (I) | Treatment −I | Treatment +I | Percent Inhibition |
|---|---|---|---|---|
| (1) None(control) | None | 0 | | |
| (2) Polycyclic Aromatic Hydrocarbons(PAH's) | | | | |
| Benzo[a]pyrene | DAGDL | 7.73 | 2.62 | 76 |
| 7,12-Dimethylbenz[a]anthracene | DAGDL | 4.83 | 1.10 | 77 |
| 7,12-Dimethylbenz[a]anthracene | CGT | 4.80 | 0.81 | 83 |
| 7,12-Diemthylbenz[a]anthracene | PGT | 6.42 | 2.25 | 65 |
| 7,12-Diemthylbenz[a]anthracene | EGL | 6.42 | 2.12 | 67 |
| 3-Methylcholanthrene | CGT | 5.62 | 3.32 | 43 |
| (3) Nitro-PAH | | | | |
| 1-Nitropyrene | CGT | 5.30 | 2.65 | 50 |
| (4) Aromatic Amines | | | | |
| 2-Acetylaminofluorine | DAGDL | 5.11 | 1.73 | 66 |
| 2-Naphthylamine | CGT | 3.29 | 1.67 | 49 |
| (5) Hydrazine | | | | |
| 1,2-Dimethylhydrazine | CGT | 5.40 | 2.20 | 60 |
| (6) N—Nitroso-compounds | | | | |
| N—Nitrosodimethylamine | CGT | 3.40 | 0.81 | 76 |
| N—Nitrosodiethylamine | CGT | 4.21 | 2.48 | 41 |
| N—Nitrosodibutylamine | CGT | 5.44 | 2.55 | 53 |
| N—Nitrosomethylurea | CGT | 4.69 | 1.45 | 69 |
| N—Nitrosoethylurea | CGT | 4.50 | 1.44 | 68 |
| (7) Fungal Toxins | | | | |
| Aflatoxin $B_1$ | CGT | 4.37 | 0.62 | 86 |
| Aflatoxin $G_2$ | CGT | 3.80 | 1.41 | 70 |
| (8) Benzodioxole | | | | |
| Safrole | CGT | 5.90 | 3.60 | 45 | a The total concentration (net units of 60 kd factor activity) was obtained by summating the percent nuclear cpm transported in each fraction of the 60 kd region of the Sepharose CL-6B profile and subtracting the unit in the corresponding region of the normal (control) rat plasma profile. One unit is equal to the percent nuclear counts transported in RNA from 30 min. $^{14}C$—orotate prelabeled nuclei during a 30 min. incubation in the reconstituted cell-free system. The β-glucuronidase inhibitors (I) tested were as follows: 2,5-di-O—acetyl-D-glucaro-1,4:6,3-dilactone (DAGDL), microencapsulated D-glucaro-1,4-lactone (EGL), calcium glucurate (CGT) and potassium hydrogen glucarate (PGT).

EXAMPLE II

Example II relates the effects of a D-glucaro-1,4-lactone precursor, calcium glucarate (CGT), on the promotion phase of 7,12-dimethylbenz[a]anthracene (DMBA)-induced mammary tumorigenesis in female rats of the Sprague Dawley strain. The inhibitory effect of CGT on the chemical carcinogen-mediated induction of the 60 kd oncofetal protein associated with carcinogenesis and tumorigenesis is described in the Example I. CGT is a more natural, slow or sustained release precursor of D-glucaro-1,4-lactone.

Fifty day old female Sprague Dawley rats were utilized in these experiments. For induction of mammary tumors the rats received a single dose of 130 mg/kg of DMBA in sesame oil by gavage. Animals pretreated with CGT received 4.5 mmoles/kg of CGT in sesame oil at 3 hours and again at 0.5 hours before administration of the carcinogen. This protocol tests the inhibitory effect of CGT on the initiation phase. Alternatively, the rats were fed a standard chow diet supplemented with 10% CGT (w/w). To evaluate the effect of CGT on the promotion phase the rats were changed from the chow diet to the CGT supplemented diet two weeks after treatment with DMBA. One mole of glucarate is converted to approximately one-third of a mole of GL in an equilibrated aqueous solution.

At the time periods indicated above blood samples were obtained from rats under ether aneathesia by cardiac puncture, the serum was then prepared and assayed for β-glucuronidase activity using a commercial diagnostic kit sold by Sigma Chem. Co., St. Louis, MO. The GL-induced inhibition observed could be reversed by removing the inhibitor from the enzyme by prolonged dialysis. Dilution or short dialysis of the serum obtained from animals treated with the β-glucuronidase inhibitors had no effect on the degree of inhibition of β-glucuronidase due the high affinity of the inhibitor for the enzyme.

The estradiol content of the serum was measured using a radio-immuno assay as described in Goldman, P., et al., Cancer Let., 1985; 25:277–282. The urine was assayed for 17-ketosteroids using a commercial diagnostic kit sold by Sigma Chem. Co., St. Louis, MO. Estradiol content is expressed as pg/ml, while 17-ketosteroids are given as $\mu$g/100 gm body weight/24 hour excretion.

The mammary tumors were measured with micrometer calipers. Two measurements were taken, the longest dimension and dimension at right angles to this parameter.

In the long term feeding experiments in which CGT intake was over an extended period of time, at the termination of the experiment the following organs were examined macroscopically and weighed: liver, kidneys, adrenals.

Figure 5:
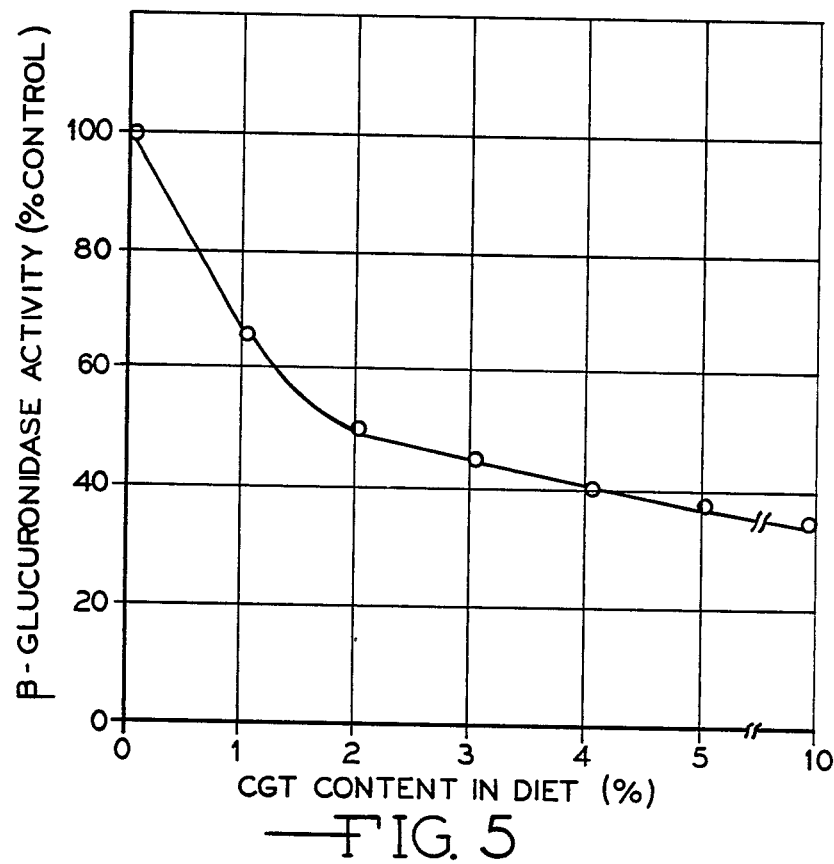
FIG. 5 is a graph showing the effect of dietary CGT on serum $\beta$-glucuronidase activity in the rat.

For the inhibition of the initiation stage, CGT was given by gavage in two doses (4.5 mmoles/kg/dose) at 3 hours and again at 0.5 hours before carcinogen administration. CGT added to a regular rat chow diet at a concentration of 2.0% reduces serum β-glucuronidase levels in female Sprague Dawley rats by 50%. FIG. 5 shows the effect of dietary CGT or serum β-glucuronidase activity in the rat. The concentrations of CGT were incorporated into the powdered chow diet. The blood samples were obtained 10 days after the initiation of the CGT feeding. This reduced level is similar to the level of female rats of the Long Evans strain, known to be at less risk as compared to rats of the Sprague Dawley strain to mammary carcinogenesis.

Figure 6:
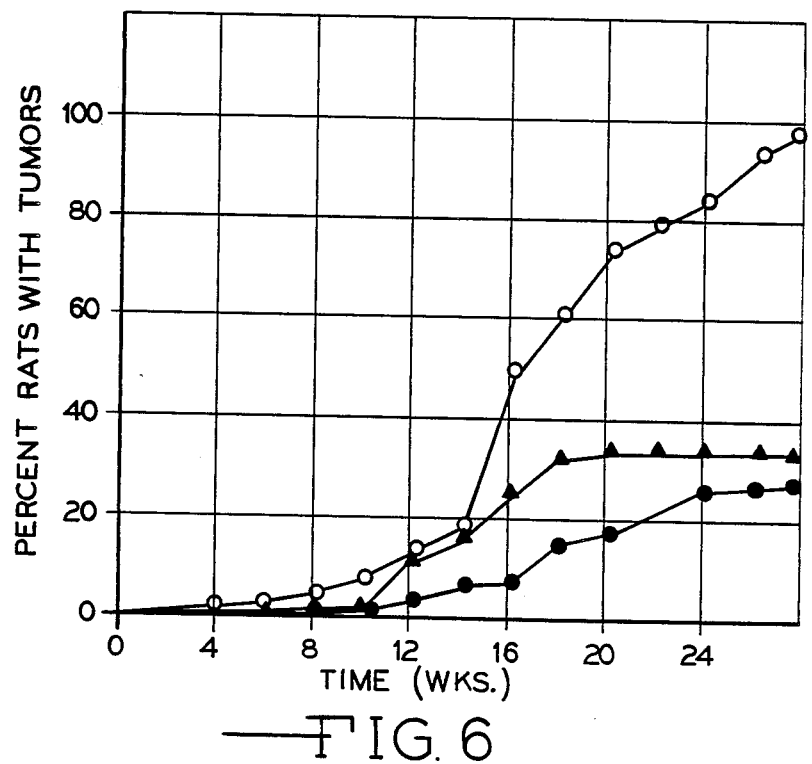
FIG. 6 is a graph showing the effect of CGT on the initiation ●—● and promotion (▲—▲) phases of DMBA-induced mammary tumorigenesis in rats (O—O) controls).

The data in FIG. 6 show that a diet containing CGT significantly inhibits the promotion phase of DMBA-induced mammary carcinogenesis. The rats did not receive any $\beta$-glucuronidase inhibitor until 2 weeks post-treatment with DMBA. At this time, the rats were transferred from a chow diet to a chow diet supplemented with 10% CGT. This diet was continued until the termination of the experiment. The results obtained when the rats were maintained on a chow diet both before and after DMBA-treatment (control) or when they were only pretreated with CGT at 3 hours and 0.5 hours before DMBA treatment are shown for comparative purposes. Three groups each, with eighteen 50 day old rats, were given intragastrically a single dose of 20 mg of DMBA in 1.0 ml of sesame oil. One group (●—●) received 4.5 mmoles/kg of CGT by stomach tube at 3 hours and again at 0.5 hours before DMBA. A second (control) group (O—O) received vehicle (i.e. sesame oil) only at the same two time periods. Both of these groups were then put on regular chow diet. The third group of rats (▲—▲) did not receive any pretreatment before administration of DMBA. Essentially all rats with tumors in the CGT diet supplemented group had only one tumor per rat.

The data in FIG. 6 show that by 28 weeks tumor induction in the rats on the CGT diet was only 30% of that in the controls and similar to the group which received CGT only during the initiation phase. Thus, CGT has a dramatic effect on the promotion phase in this particular model. Further, although 10% CGT was used in this experiment, a 2% CGT diet would also be as effective. It should be noted that rats on both the 2% and 10% CGT diets ate quantities of food and had a weight-gain essentially identical to those on chow diet.

The anti-promotional effect of CGT in DMBA-induced mammary tumorigenesis is due to the reduction in the steady-state level of the sex hormones. The data in Table 2 show that female rats on a CGT diet had reduced steroid hormone levels. Thus the serum estradiol and urinary 17-ketosteroid levels were reduced 24% and 55% respectively. In this model system mammary tumors remain hormone-responsive for at least 28 days following a single carcinogenic dose of DMBA. It is significant that estradiol levels in 60–65 day old female Sprague Dawley rats are significantly higher than in Long Evans female rats of the same age. The lower level of estradiol in the Long Evans strain accounts in part for the relatively higher resistance, as compared to the Sprague Dawley strain, to DMBA-induced mammary tumoringenesis. Thus, the level of steroid hormones including estradiol in the Sprague Dawley strain can be reduced and resistance to DMBA-induced mammary carcinogenesis increased by supplementing the diet with CGT.

With reference to FIG. 6 the 70% reduction in percentage of rats with tumors when the rats were fed diet supplemented with CGT was an average, the net rate of formation and regression of tumors having reached an equilibrium between 18 and 28 days. Thus in contrast to DMBA-treated rats on chow diet, some tumors on the chow diet supplemented with 10% CGT undergo regression. Table 3 summarizes the effect of 10% CGT in the diet on DMBA-induced tumors which escape the anti-promoter effects of CGT. The data indicate that CGT caused a significant regression of these tumors, as a consequence of the reduction of sex hormone levels. Hormone-responsive tumors undergo regression by hormone-deprivation, or by hormone excess. Many carcinogen-induced mammary carcinomas in the rat undergo marked regression following hypophysectomy or ovariectomy. Significantly, the overall tumor incidence (i.e., 33%) in the group of rats receiving 10% CGT supplemented diet, beginning 2 weeks post-DMBA treatment, is similar for rats ovariectomized 2 weeks after DMBA treatment i.e. 35% tumor incidence. Thus the overall tumor incidence in the later stages is a composite of both the promotion phase and tumor regression (14%-reduction of the overall tumor incidence due to tumor regression was observed).

At the end of 28 weeks on the CGT-chow diet, with or without DMBA treatment the rats were necropsied and several organ weights were compared with those of age/weight matched controls on chow diet. The livers and kidneys were essentially identical in weight in all animals. The adrenals were slightly (ca 20%) smaller by weight in the group receiving 10% CGT supplemented chow.

The promotional phase of tumor formation in experimental carcinogenesis is dramatically inhibited, or slowed, by supplementing the diet with a non-toxic $\beta$-glucuronidase inhibitor. Since, with the exception of dietary fat normally present in the chow diet, no exogenous promoters were knowingly administered, and, as shown by the present invention, the reduction is due, in part, to increased clearance of steroid sex hormones as glucuronides. The serum level of these hormones is reduced to a level comparable to those of young rats of strains more resistant to chemical mammary carcinogenesis.

In addition to inhibiting or delaying mammary tumor formation when given chronically in the diet, after the initiation phase, CGT also induces regression of some of the tumors which formed. Thus as shown in FIG. 6, the plateau in the number of CGT-fed rats with tumors reached at 18 weeks post-treatment, represents an equilibrium between the number of tumors growing and regressing.

Thus, CGT is an ideal slow release precursor of GL which is the natural inhibitor or regulator of $\beta$-glucuronidase.

TABLE 2

Effect of CGT on Estrogen and Androgen Levels in 50 Day Old Sprague Dawley female rats

| Hormone | Hormone Level | |
| --- | --- | --- |
| | −CGT | +CGT |
| Estradiol (serum)[a] | 51 | 39 |
| 17-Ketosteroids (urinary excretion)[b] | 29 | 13 |

[a] pg/ml.
[b] μg/100 g body wt × 24 hrs.

TABLE 3

Effect of 10% CGT-diet on DMBA-induced Mammary Tumor Regression

| | Average Tumor Volume[cm³] | | | | |
| --- | --- | --- | --- | --- | --- |
| Group | 16 wks | 20 wks | 24 wks | 28 wks | 32 wks |
| Normal diet | 2.80±0.50 | 3.00±0.70 | 3.25±0.75 | 3.50±0.91 | 3.82±0.53 |
| 10% CGT diet | 2.82±0.57 | 2.17±0.76 | 1.87±0.87 | 1.20±0.82 | 1.20±0.77 |

EXAMPLE III.

The extreme toxicity of TCDD (dioxin) may derive from tissue damage or biochemical changes wrought during the initial exposure and/or to significant retention of the TCDD, with slow release of the TCDD from certain organs, particularly adipose tissue. Certain toxic xenobiotics may be detoxified (sequestered) by glucuronidation, then removed from the body. Consequently, alterations in the ratio of detoxification/retention will affect toxicity. Since glucuronyl-transferase, which catalyzes glucuronidation, and β-glucuronidase which catalyzes deglucuronidation, appear to be present in all animal tissues, factors which alter the ratio of activity of the two enzymes, alter the susceptibility of the animal to toxic xenobiotics which undergo glucuronidation. The susceptibility of mammals to TCDD, which is known to be glucuronidated, may be altered by inhibiting β-glucuronidase. D-glucaro-1,4-lactone (GL) is a normal endogenous inhibitor of β-glucuronidase. Calcium glucarate (CGT), when given orally, is a slow release form of GL.

Figure 7A:
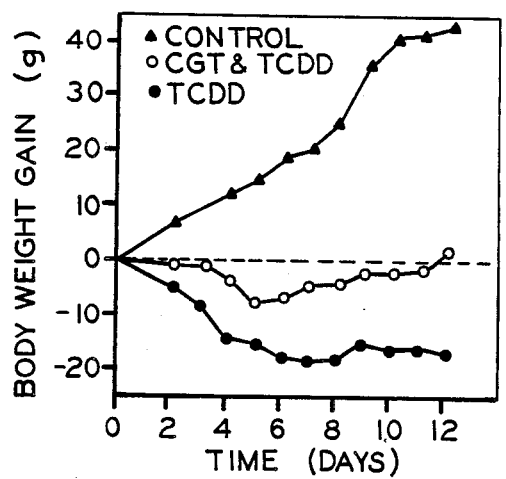
FIG. 7a,b, and c, are graphs showing the effect of CGT on (a) body weight gain, (b) food intake, and (c) water intake of rats treated with TCDD.
Figure 7B:
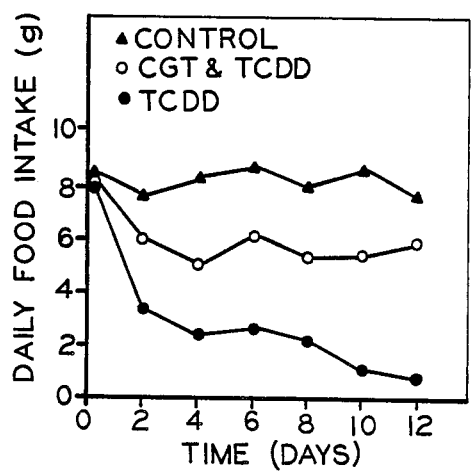
Figure 7C:
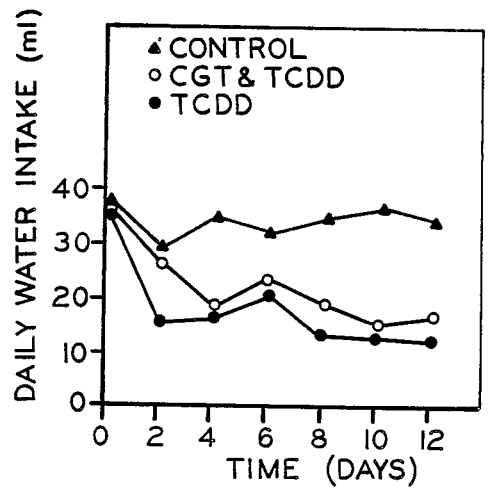

TCDD was administered i.p. in a single dose of 40 μg/kg in sesame oil (0.5 ml) to 125 gm female Sprague Dawley rats. One group of 4 rats received 2 doses of CGT (4.5 mmole/kg) in sesame oil (1.0 ml) by stomach tube at 3 hours and a second dose at 0.5 hours before treatment with TCDD. A second, TCDD-treated group received oil only in place of the CGT. Control rats received oil only by stomach tube and i.p. injection. Thereafter, the weights and water and food consumption were recorded and the results demonstrating a definite anti-"TCDD toxicity" effect of CGT are shown in FIGS. 7a–7c.

EXAMPLE IV

PAH glucuronides are believed to be true detoxication products. They may also act as carriers and be transported to target tissues, cleaved there by β-glucuronidase and then become available for further metabolic activation to ultimate carcinogens. Since both glucuronyl transferase, which catalyzes glucuronidation, and β-glucuronyltransferase, which catalyzes de-glucuronidation, are present in all mammalian tissues, any factor which alters the ratio of activity of the two enzymes may alter susceptibility of the target tissue to carcinogenic PAHs.

Example IV illustrates the inhibition of PAH-mediated carcinogenesis by inhibiting de-glucuronidation with 2,5-di-O-acetyl-D-glucaro-1,4:6,3-dilactone (DAGDL).

The carcinogenicity of benzo[a]pyrene (BP) in rats is reduced by the use of DAGDL. BP is a much studied powerful PAH carcinogen, common in the environment and known to undergo glucuronidation both in vitro and in vivo after metabolic activation. Two short-term tests for carcinogenicity are used to assess the anti-carcinogenic potential of DAGDL. One of them is in vivo covalent DNA binding which is recognized as a quantitative indicator of chemical carcinogenesis. A second test for carcinogenicity, the appearance and concentration in circulation of the carcinogen-treated animal of a 60 kd oncofetal protein is also used. The 60 kd oncofetal protein is detectable in liver cytosol within 40 hours after a single dose of hepatocarcinogen. It is detectable in the plasma slightly later and is maximal at approximately 21 days whereupon it drops toward zero unless a tumor develops, in which case it increases more or less in parallel with tumor growth. This oncofetal protein is present in embryonic tissue and is also found in the amniotic fluid, though it does not cross the placental barrier. Example IV also illustrates ability of various carcinogenic and non-carcinogenic PAHs to induce the 60 kd oncofetal protein.

Commercially obtained [$^{14}$C]BP was diluted with carrier BP to a final specific activity of 23.6 mCi/mmol and injected intraperitoneally into fifty day old female Sprague Dawley rats at a dose of 7.9 μmol/kg body weight in 0.5 ml of sesame oil. Experimental rats were pretreated 0.5 hours earlier with one dose of 1.5 mmol/kg body weight of DAGDL which was administered by stomach tube as a suspension in 1.0 ml of sesame oil, while control rats received the vehicle only. The experimental and control group contained 2 rats each. Heart, kidney, liver, lung and mammary gland were removed under ether anesthesia 48 hours post-administration of BP. The DNA was isolated immediately and purified by chloroform phenol extraction of organ homogenates. In the case of mammary gland, the homogenate was treated with collagenase II. Following purification with ribonuclease A and protease K, the DNA concentration was estimated by U.V. absorption and the bound radioactivity was determined by radioassay in liquid scintillant.

The following PAHs and their derivatives were administered i.p. in 0.5 ml of sesame oil to experimental rats, while control rats received the vehicle only. BP and benzo[e]pyrene were administered at a dose of 210 μmol/g body weight. Anthracene, benzo[a]anthracene 7,12-dimethylbenz[a]anthracene, fluroene, 2-fluoro-7,12-dimethylbenz[a]anthracene, 3-methyl-1,2-dihydrobenz[j]aceanthrylene (3-methylcholanthrene) and pyrene were administered at a dose of 160 μmol/kg. 1-Nitropyrene was administered at a dose of 105 μmol/kg. These are carcinogenic doses. Non-carcinogens were administered in doses equimolar to the corresponding carcinogens.

DAGDL (1.5 mmol/kg body weight was administered by stomach tube in 1.0 ml of sesame oil 0.5 hour before and again at 2.5 hours after BP. The controls received 1 ml of the vehicle at the same time.

Twenty-one days post-administration of PAH, blood was obtained from the rats under light ether anesthesia by cardiac puncture using heparinized syringes. Following removal of the cellular components the plasma was stored frozen until testing. The 30–60% ammonium sulfate fraction of the plasma was dialysed against TMK buffer (50 mM Tris-HCl pH 7.5, 25 mM KCl and 2.5 mM MgCl$_2$) and fractionated on a column of Sepharose CL-6B (1.6×90 cm) equilibrated with the same buffer. Three ml fractions were collected and 200 μl aliquots were assayed in the reconstituted cell-free system for RNA transport activity.

The cell-free system for RNA transport consists of 50 mM Tris-HCl, pH 7.85 at 20° C. (final assay pH is 7.45 at 30° C.), 25 mM KCl, 2.5 mM MgCl$_2$, 0.545 mM CaCl$_2$, 4.5 mM spermidine, 1.8 mM dithiothreitol, 2.5 mM Na$_2$HPO$_4$, 170 mM sucrose, 2.0 mM ATP, 3.5 mM phosphoenolpyruvate, 0.3 mM GTP, 0.41 mg/ml methionine, 4.4 mM (NH$_4$)$_2$SO$_4$ added as a component of 35 units of pyruvate kinase, 5×10$^6$ prelabeled nuclei per ml of medium and 5 mg/ml of dialysed cytosol. Yeast RNA (500 g/ml) is added as ribonuclease inhibitor. The nuclei are prelabeled in vivo for 30 minutes with [$^{14}$C]-orotic acid. This mixture (800 μl), with addition of 200 μl of a fraction from the Sepharose CL-6B column or TMK buffer, is incubated at 30° C. for 30 minutes before pelleting the nuclei and precipitating the RNA from the supernatant for radioassay. The RNA transport activity assayed by this biochemical assay, is expressed in units, where one unit is percentage of increase in RNA release upon addition of 200 μl of a fraction from the Sepharose CL-6B column. All results are directly comparable since an identical amount (85 mg) of the 30-60% ammonium sulfate fraction of the plasma protein was loaded on the Sepharose CL-6B column. After plotting the activity of the various fractions the total units in the 60 kd region were estimated.

Figure 8:
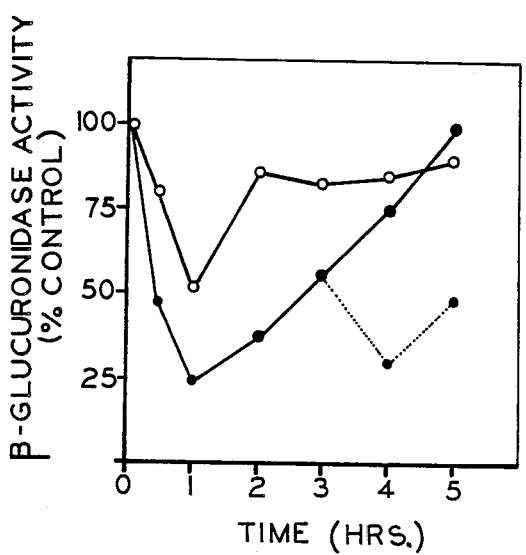
FIG. 8 is a graph showing the effect of a single dose (1.5 mmol/kg of GL (O—O) and DAGDL (●—●) on rat serum β-glucuronidase activity; the effect of a second dose of DAGDL given to rats at 3 hour (●—●) is also shown.

DAGDL or GL (1.5 mmol/kg) in 1.0 ml of sesame oil, or vehicle only (controls) was administered to rats by stomach tube at zero time. At specified times, as shown in FIG. 8, blood samples were obtained from different rats by cardiac puncture under ether anesthesia. The serum was prepared and assayed for β-glucuronidase activity using a commercial diagnostic kit sold by Sigma Chemical Company, St. Louis, MO. The assay is based on the hydrolysis of phenolphthalein-glucuronide and quantitation of phenolphtalein in alkaline medium at 550 nm.

The superiority of DAGDL over GL is readily apparent from the time-course inhibition of serum β-glucuronidase after giving single doses to rats. As seen in FIG. 8, 1.5 mmol/kg of GL transiently depresses the serum β-glucuronidase approximately 50% at 1 hour after administration, but it rapidly rises back to the pre-treatment level. In contrast the same concentration of DAGDL rapidly achieves a 50% inhibition of serum β-glucuronidase within 0.5 hour of administration and this level of inhibition, or greater, is maintained for approximately 3 hours after administration. Also shown by the broken line is the effect on serum β-glucuronidase of administering a second dose of DAGDL at 3 hours.

The data in Table 4 demonstrate that pre-treatment of rats with a single dose of DAGDL inhibited the in vivo binding of [$^{14}$C]BP to DNA in the 5 potential target tissues tested. In this experiment 50 day old female rats of the Sprague Dawley strain received 1.5 mmol/kg of DAGDL 0.5 hours before the intraperitoneal injection of 7.9 μmol/kg of [$^{14}$C]BP. The DNA was extracted from the tissues and radioassayed by established procedures.

The covalent binding indices shown for the tissues of the control animals are as expected, as reported in Lutz, W. K., *Mutation Res.*, 1979; 65:289-356 and Lutz, W. K., et al., *Cancer Res.*, 1978; 38:575-578. However, the [$^{14}$C]BP binding was markedly reduced in the rats pre-treated with DAGDL, varying from 44% of the control value in heart and 47% in mammary gland to as high as 72% in the lung. The exceptionally high degree of inhibition of binding BP in the lung is of importance since the lung is one of the important routes of exposure to BP.

TABLE 4

Effect of DAGDL On In Vivo Binding of BP To Organ DNA[a].

| Organ | Covalent Binding Index[b] | | |
|---|---|---|---|
| | −DAGDL | +DAGDL | Inhibition (%) |
| Heart | 18 | 10 | 44 |
| Kidney | 39 | 12 | 69 |
| Liver | 24 | 9 | 63 |
| Lung | 30 | 8 | 72 |
| Mammary gland | 38 | 20 | 47 |

[a]Data shown are average of 2 rats which agreed to within 10%
[b]Calculated according to Lutz, 1979, supra.

A second criterion used for the ability of DAGDL to reduce the overall exposure of tissues to administered carcinogens, is the induction of a 60 kd oncofetal protein. This protein is assayed 21 days post-treatment with the carcinogen when the transient induction is maximal. Prior to assay the activities in the plasma are separated according to size on a Sepharose CL-6B column. This procedure separates the 60 kd factor from similar activities with molecular weights of 700 kd and 35 kd normally found in the plasma of untreated rats. These factors are all assayed by their ability to induce the transport of RNA (mainly mRNA) from isolated nuclei in a cell-free system.

Figure 9:
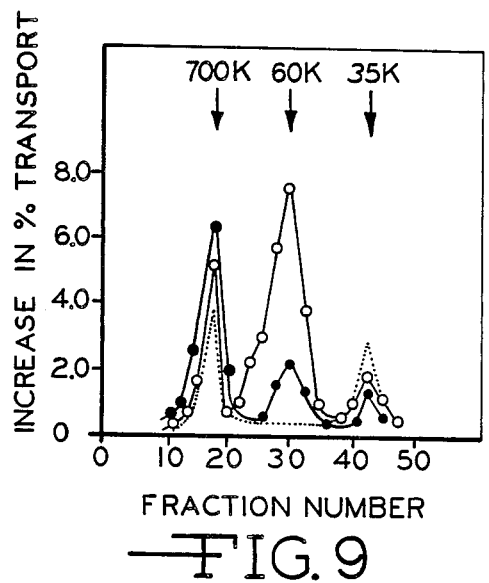
FIG. 9 is a graph showing Sepharose CL-6B profiles of the RNA transport activities in the plasma of rats at 21 days post-treatment with BP (160 μmol/kg, i.p. in 0.5 ml of sesame oil) with (●—●) or without (O—O) concurrent treatment with DAGDL (two doses, 1.5 mmol/kg each in 1 ml of sesame oil given intragastrically 0.5 hour before and 2.5 hour after the carcinogen); plasma from a normal rat (---) is shown for comparison.

Shown in FIG. 9 are the Sepharose CL-6B size distribution profiles of the RNA transport activities in the plasma of rats, 21 days post-treatment with BP, with or without concurrent treatment with DAGDL. In this series of experiments the treated rats received 2 doses of DAGDL, one 0.5 hour before and a second 2.5 hour after the BP; controls received the vehicle only. The data show that the 60 kd factor is absent from normal rat plasma but is present in the plasma from BP-treated rats. Furthermore, the concentration is 4-fold lower in the plasma of rats treated with DAGDL. These results represent a composite picture of the effect of BP on the whole organism. The 60 kd factor is induced in the target cells of carcinogen-treated animals, then released by some mechanism to the blood.

TABLE 5

Ability of PAHs and Their Derivatives To Induce The 60 kd Oncofetal Protein In Vivo.

| Compound | Plasma Concentration of the 60 kd Protein at 21 days Post-treatment with PAH[a] |
|---|---|
| Known Carcinogens | |
| Benz[a]anthracene | 4.92 |
| Benzo[a]pyrene | 7.73 |
| Benzo[e]pyrene | 3.37 |
| 7,12-Dimethylbenz[a]anthracene | 6.42 |
| 3-Methyl-1,2-dihydrobenz[j]aceanthrylene | 6.82 |
| 1-Nitropyrene[c] | 5.30 |
| Known Non-Carcinogens | |
| Anthracene | 0.0 |
| Fluorene | 0.0 |
| 2-Fluoro-7,12-dimethylbenz[a]anthracene | 0.0 |
| Pyrene | 0.0 |

[a]The total concentration (units) as obtained by summing increase in percent RNA transport in each fraction of the 60 kd peak in the Sepharose CL-6B profile (see Fig.) If labeled RNA release was 2% or less of the nuclear counts, then plasma concentration of the 60 kd protein is indicated as 0.0. The background release was 1.90 ± 0.12%.

The data in FIG. 9 is confirmed by the data in Table 5, which compares the ability of carcinogenic and non-carcinogenic PAHs to induce the 60 kd factor. PAHs were administered to 50 day old female rats of the Sprague Dawley strain. All PAHs were tested at a dosage of 105-210 μmol/kg and all were injected intraperitoneally. Thus all six carcinogenic PAHs tested caused significant induction of the 60 kd factor while none of the non-carcinogenic PAHs induced the 60 kd oncofetal protein. These data indicate that this 60 kd protein induction is very specific for carcinogens.

GL, when administered to rats at a dose of 1.5 mmol/kg, provides only a transient inhibition of β-glucuronidase in the blood. In comparison, the equimolar dose of DAGDL gives a marked and prolonged inhibition of the enzyme. The DAGDL-mediated inhibition of β-glucuronidase is not influenced significantly by co-administration of a carcinogen by any route of administration. A second dose of DAGDL administered 3 hours after the initial dose and 2.5 hours after a carcinogen administration prolongs the marked, approximately 50% inhibition of β-glucuronidase up to 6 hours.

It is during the early period of exposure to carcinogens that DAGDL has its greatest anticarcinogenic effect. PAHs, after metabolic activation, are detoxified through extensive coupling with glucuronic acid and then excreted in bile and to a much lesser extent in urine. When BP is administered to rats i.v. at a dose of 3 μmol/kg, some 60% of the dose is excreted in bile in 6 hours. The biliary metabolites are mainly polar conjugates, 40% of them being glucuronides.

The overall inhibition of PAH-mediated carcinogenesis, as reflected by the inhibition of the 60 kd oncofetal protein induction, ranges from 50% for both 1-nitropyrene and 3-methylcholanthrene, to 75% for BP and DMBA.

EXAMPLE V

The effect of DAGDL on the acute toxicity and the early phase of N-Methylnitrosourea (MNU) - induced chemical carcinogenesis is shown in Example V. Table 6 below shows the relative inhibitory effect of DAGDL on the induction of the 60 kd oncofetal protein by MNU. The data represent estimates of the activity of the 60 kd protein 21 days after the carcinogen administration. The inhibitor was administered according to a 2 dose regiment. The inhibitor was given by stomach tube; MNU was injected intraperitoneally.

TABLE 6

Effect of DAGDL on MNU-induction of the 60 kd factor in plasma of S.D. female rats.

| Carcinogen | Inhibitor | Units |
|---|---|---|
| 1. None | None | 0 |
| 2. N—methylnitrosourea (N—MNU, 440 μmole/kg) | None | 4.6 |
|  | DAGDL (2 × 1.5 mmole/kg) | 1.2 |

These data illustrate that MNU forms an, as yet, unidentified hydroxylated intermediate. A marked, approximately 100 g difference in toxicity-induced weight loss of DAGDL-treated and non-treated rats, 21 days after treatment with MNU was also observed. This difference illustrates that DAGDL pre-treatment reduces the acute toxicity of MNU.

EXAMPLE VI

Figure 10:
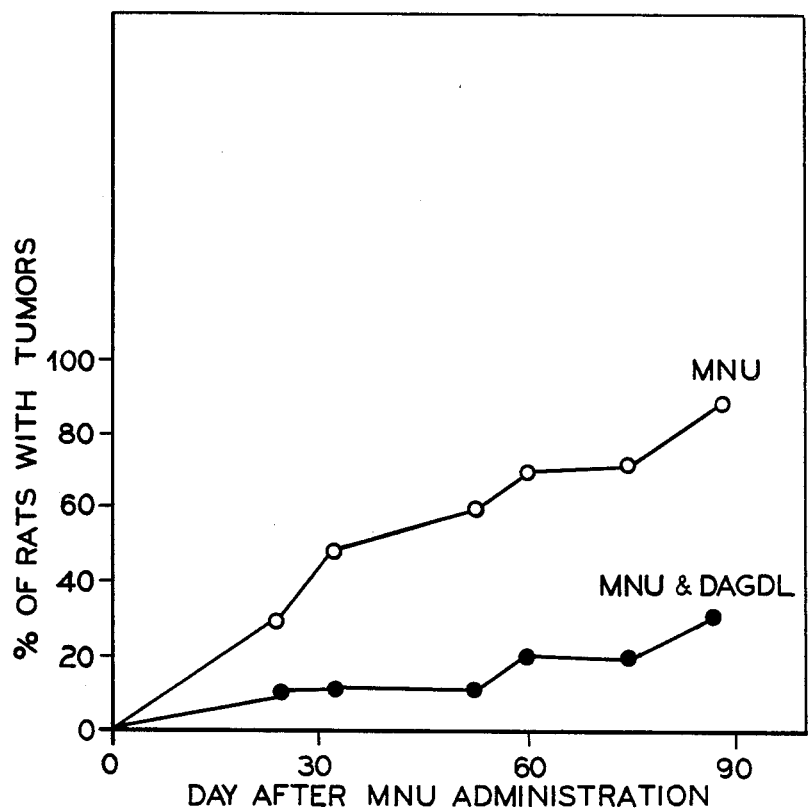
FIG. 10 is a graph showing the effect of DAGDL on MNU-induced mammary tumorigenesis in the rat.

Inhibition by DAGDL of carcinogenesis by N-methylnitrosourea (MNU) is shown in Example VI. DAGDL is a potent inhibitor of MNU-induced mammary carcinogenesis in the rat model. In this experiment, MNU (40 mg/kg) was administered to 50 day old Sprague Dawley female rats by i.v. injection. One half of the rats were co-administered DAGDL according to a 2 dose schedule. The results, summarized in FIG. 10, show that DAGDL caused a dramatic (approx. 4-fold) inhibition of mammary tumor development in these animals.

Although the degree of glucuronidation of MNU intermediates is not known, it is known that some nitrosamines and specifically N-nitrosodibutylamine, are metabolized in vivo to give several hydroxyl-derivatives and that some of them undergo glucuronidation.

EXAMPLE VII

The tumor-inducing potential of hormones in endocrine-related organs of experimental animals is known. In particular, a relationship has been shown between hepatic tumors and estrogen use in women who have a history of prior oral contraceptive use. In contrast to usual relatively benign nature contraceptive (estrogenic) induced tumors, liver tumors associated with the use of anabolic steroids are usually malignant, especially when the androgen content of the hormonal preparation is high. At the present time, anabolic, androgenic, and estrogenic hormones are used widely for a variety of clinical indications. It has been illustrated by others that estrogens and androgens promote the carcinogenic effects of various procarcinogens, but that they alone are not intrinsically carcinogenic. Regardless of the mechanism of their action an excess of estrogens and/or androgens or an imbalance in their levels may induce some cancers. Table 7 illustrates that the 1.5% DAGDL diet reduces sex hormone levels in male and female rats.

TABLE 7

Effect of DAGDL on Estrogen and Androgen Levels in Sprague Dawley Rats

| Hormone | Hormone Level | |
|---|---|---|
|  | −DAGDL | +DAGDL |
| Females |  |  |
| Estadiol (serum)[a] | 180 | 140 |
| 17-Ketosteroids (urinary excretion)[b] | 30 | 12 |
| Males |  |  |
| Testosterone (serum)[c] | 19 | 9 |
| 17-Ketosteroids (urinary excretion)[b] | 42 | 17 |

[a] pmol/liter
[b] μg/100 g body wt × 24 hrs.
[c] nmol/liter

A lower steady state level of steroid hormones is observed after DAGDL administration. The adrenals are also slightly (ca 20–30%) smaller by weight in the group receiving supplemented chow. This indicates that DAGDL, and other GL-based de-glucuronidation inhibitors, affect the secretion of steroid hormones of both testicular/ovarian and adrenal origin.

DAGDL, CGT and other GL-based de-glucuronidation inhibitors are thus useful in prevention and/or treatment of steroid hormone-dependent cancers as well as other diseases caused by steroid hormone disorders.

EXAMPLE VIII

Figure 11:
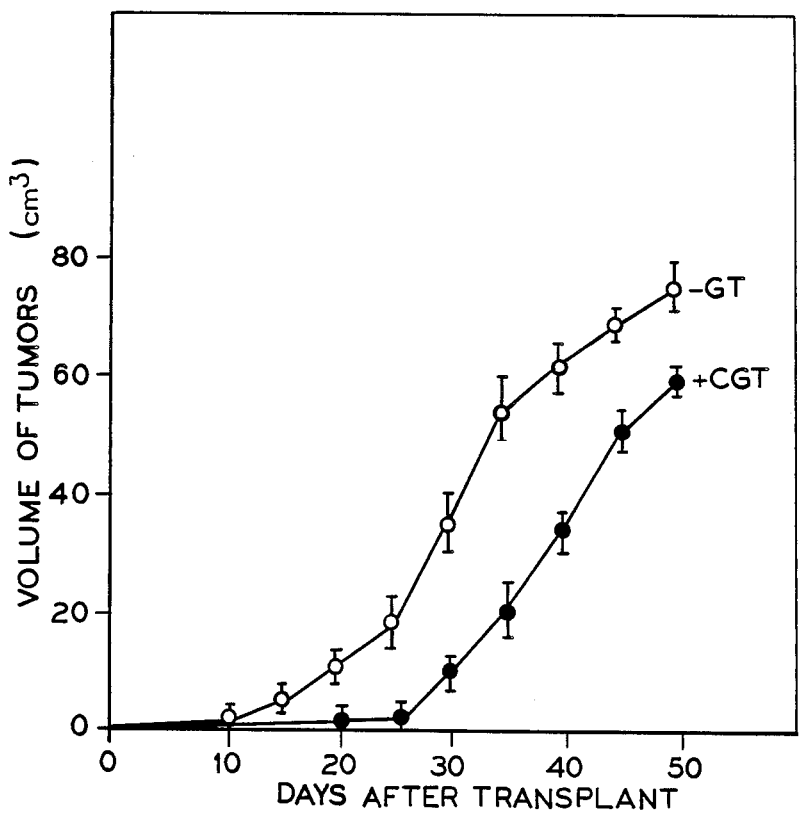
FIG. 11 is a graph showing the effect of dietary CGT on the growth of a transplantable tumor (Morris Hepatoma 7777).

The effect of CGT on the growth of the Morris Hepatoma 7777 is shown in Exmaple VIII. One group of male Buffalo rats was put on 2% CGT diet one week before the hepatoma transplant, while the other group of rats (controls) was kept on the regular chow diet. A minimum number of Morris Hepatoma 7777 cells consistent with tumor growth were innoculated subcutaneously in the left flank of all rats. Tumor diameters were measured at least twice weekly, and tumor volume was calculated. The results are shown in FIG. 11. In the CGT-treated group, tumors started to grow approximately two weeks later, and their growth was slightly slower than those in the control group.

As will be evident to those skilled in the art, various modifications of this invention can be made or followed in light of the foregoing disclosure and discussion without departing from the spirit and scope of the disclosure or from the scope of the claims.

We claim:

1. A method for inhibiting the activity of β-glucuronidase in a mammal which comprises the administration to the mammal of an effective amount of a water insoluble, or sparingly soluble, sustained release precursor of D-glucaro-1,4-lactone (glucarolactone) selected from the group consisting of calcium D-glucarate, potassium hydrogen D-glucarate or microencapsulated glucarolactone.

2. A method of treating animals and humans in need of a β-glucuronidase inhibitor which comprises administering to such animals and humans a composition the essential active constituent of which is a water insoluble or sparingly soluble sustained release precursor of glucarolactone selected from the group consisting of calcium D-glucarate, potassium hydrogen D-glucarate or microencapsulated glucarolactone and their pharmaceutically acceptable salts, said composition being administered in an amount to provide an effective dosage of the compound and the composition containing, in addition to the compound, a pharmaceutical vehicle therefor.

3. A therapeutic composition in dosage form comprising an orally administrable pharmaceutical carrier and a compound selected from the group consisting of calcium D-glucarate, potassium hydrogen D-glucarate, or microencapsulated glucarolactone.

4. A method of reducing the toxic effects of chemicals which comprises the administration to a patient at least one sustained release precursor of glucarolactone selected from the group consisting of calcium D-glucarate, potassium hydrogen D-glucarate or microencapsulated glucarolactone, said sustained release precursor being insoluble or only sparingly soluble in water at pH 5–7 but going into solution at pH 1–4, said sustained release precursor inhibiting the activity of the β-glucuronidase enzyme such that de-glucuronidation is prevented and said toxic chemicals are thereby excreted by the patient.

5. A method of preventing the initiation of carcinogenesis which comprises the administration to a patient at least one sustained release precursor of glucarolactone selected from the group consisting of calcium D-glucarate, potassium hydrogen D-glucarate or microencapsulated glucarolactone, said sustained release precursor being insoluble or only sparingly soluble in water at pH 5–7 but going into solution at pH 1–4, said sustained release precursor inhibiting the activity of the β-glucuronidase enzyme such that de-glucuronidation is prevented.

6. A method of preventing promotion of carcinogenesis and tumorigenesis which comprises the administration to a patient at least one sustained release precursor of glucarolactone selected from the group consisting of calcium D-glucarate, potassium hydrogen D-glucarate or microencapsulated glucarolactone, said sustained release precursor being insoluble or only sparingly soluble in water at pH 5–7 but going into solution at pH 1–4, said sustained release precursor inhibiting the activity of the β-glucuronidase enzyme such that de-glucuronidation is prevented.

7. A method of arresting growth of a tumor or causing regression of the tumor which comprises administering to a patient at least one sustained release precursor of glucarolactone selected from the group consisting of calcium D-glucarate, potassium hydrogen D-glucarate or microencapsulated glucarolactone, said sustained release precursor being insoluble or only sparingly soluble in water at pH 5–7 but going into solution at pH 1–4, said sustained release precursor inhibiting the activity of the β-glucuronidase enzyme such that de-glucuronidation is prevented.

8. The method of claims 4, 5, 6, or 7 wherein said sustained release precursor of glucarolactone is administered prior to, during, or after exposure to cancer causing agents, conditions, or chemicals.

9. The method of claim 8, wherein said sustained release precursor is administered in the form of a tablet or capsule or suspension.

10. The method of claim 8, wherein said sustained release precursor is administered in the form of an implant in the patient.

11. The method of claim 8, wherein said sustained release precursor is administered in food as food additives.

12. An orally administrable preparation of a sustained release precursor of glucarolactone selected from the group consisting of calcium D-glucarate, potassium hydrogen D-glucarate or microencapsulated glucarolactone, said sustained release presursor being such that, when provided in the form of a capsule or tablet, said sustained release precursor is slowly released in the stomach of the treated animal or human.

13. A process for the treatment of a warm blooded animal or human exposed to a carcinogenic agent which consists in administering to the living warm blooded animal or human which has acquired a toxic amount of a carcinogen, a composition comprising a sustained release precursor of glucarolactone selected from the group consisting of calcium D-glucarate, potassium hydrogen D-glucarate or microencapsulated glucarolactone which is insoluble or sparingly soluble in water at pH 5–7 but going into solution at pH 1–4 in the animal's digestive system such that said sustained release precursor inhibits the activity of β-glucuronidase in the animal or human.

14. The process of claim 13, wherein said sustained release precursor of glucarolactone is administered orally in the form of a capsule, tablet or suspension.

15. A process for the prevention of acute toxic effects of chemicals, initiation of carcinogenesis or the promotion of carcinogenesis and tumorigenesis in an animal or human which comprises orally administering an effective amount of a composition having as the essential active ingredient, a sustained release precursor of glucarolactone selected from the group consisting of calcium D-glucarate, potassium hydrogen D-glucarate or microencapsulated glucarolactone which is insoluble or only sparingly soluble in water at the pH 5–7 but going into solution at pH 1–4 said sustained release precursor inhibiting the activity of the β-glucuronidase enzyme such that de-glucuronidation is prevented.

16. A method of controlling the level of steroid hormones in a patient which comprises the administration to the patient at least one sustained release precursor of glucarolactone selected from the group consisting of calcium D-glucarate, potassium hydrogen D-glucarate or microencapsulated glucarolactone said sustained release precursor being insoluble or only sparingly soluble in water at pH 5–7 but going into solution at pH 1–4, said sustained release precursor inhibiting the activity of the β-glucuronidase enzyme such that de-glucuronidation is prevented and said level of said steroid hormones in the patient is lowered.

17. The method of claim 16, wherein said sustained release precursor of glucarolactone is administered prior to, during, or after exposure to cancer causing agents, conditions or chemicals.

18. The method of claim 17, wherein said sustained release precursor is administered in the form of a tablet or a capsule or suspension.

19. The method of claim 17, wherein said sustained release precursor is administered in the form of an implant in the patient.

20. The method of claim 17, wherein said sustained release precursor is administered in food as food additives.

21. A method of preventing the initiation or promotion of a steroid hormone-dependent disease in a patient which comprises the administration to the patient at least one sustained release precursor of glucarolactone selected from the group consisting of calcium D-glucarate, potassium hydrogen D-glucarate or microencapsulated glucarolactone said sustained release precursor being insoluble or only sparingly soluble in water at pH 5–7 but going into solution at pH 1–4, said sustained release precursor inhibiting the activity of the β-glucuronidase enzyme such that de-glucuronidation is prevented and the level of said hormones is lowered.

22. The method of claim 21, wherein said sustained release precursor of glucarolactone is administered prior to or during exposure to cancer causing agents, conditions or chemicals.

23. The method of claim 21, wherein said sustained release precursor is administered in the form of a tablet or capsule or suspension.

24. The method of claim 21, wherein said sustained release precursor is administered in the form of an implant in the patient.

25. The method of claim 21, wherein said sustained release precursor is administered in food additives.

26. A process for the treatment of a warm blooded animal or human suffering from a steroid hormone-dependent disease which consists in administering to the living warm blooded animal or human, a composition comprising at least one sustained release precursor of glucarolactone selected from the group consisting of calcium D-glucarate, potassium hydrogen D-glucarate or microencapsulated glucarolactone which is insoluble or sparingly soluble in water at pH 5–7 but going into solution at pH 1–4 in the animal's or human's digestive system such that said sustained release precursor inhibits the activity of the β-glucuronidase enzyme thereby lowering the level of said hormones in said animal or human.

27. The process of claim 26, wherein said sustained release precursor of glucarolactone is administered orally in the form of a capsule, table or suspension.

* * * * *